United States Patent
Young (10) Patent No.: US 10,849,489 B2
(45) Date of Patent: Dec. 1, 2020

(54) MEDICAL GAS DELIVERY SYSTEM

(71) Applicant: INDIAN OCEAN MEDICAL INC., Mahe (SC)

(72) Inventor: Peter Jeffrey Young, King's Lynn (GB)

(73) Assignee: INDIAN OCEAN MEDICAL INC., Mahe (SC)

( * ) Notice: Subject to any disclaimer, the term of this patent is extended or adjusted under 35 U.S.C. 154(b) by 72 days.

(21) Appl. No.: 16/079,495

(22) PCT Filed: Feb. 24, 2017

(86) PCT No.: PCT/GB2017/050506
§ 371 (c)(1),
(2) Date: Aug. 23, 2018

(87) PCT Pub. No.: WO2017/144916
PCT Pub. Date: Aug. 31, 2017

(65) Prior Publication Data
US 2019/0053698 A1 Feb. 21, 2019

(30) Foreign Application Priority Data

Feb. 24, 2016 (GB) .................................. 1603234.4
May 13, 2016 (GB) .................................. 1608473.3

(51) Int. Cl.
*A61B 1/267* (2006.01)
*A61B 1/015* (2006.01)
*A61M 16/12* (2006.01)

(52) U.S. Cl.
CPC .............. *A61B 1/267* (2013.01); *A61B 1/015* (2013.01); *A61M 16/127* (2014.02); *A61M 2202/0007* (2013.01); *A61M 2202/0208* (2013.01)

(58) Field of Classification Search
CPC ................................ A61B 1/267; A61B 1/015
See application file for complete search history.

(56) References Cited

U.S. PATENT DOCUMENTS 3,941,120 A * 3/1976 Lee ........................ A61M 16/04
600/158
4,126,127 A * 11/1978 May .................. A61M 16/0486
600/187

(Continued)

FOREIGN PATENT DOCUMENTS

CN 2100183 U 4/1992
CN 101361647 A 2/2009
(Continued)

OTHER PUBLICATIONS

Patel, et al., "Transnasal Humidified Rapid-Insufflation Ventilatory Exchange (THRIVE): a physiological method of increasing apnoea time in patients with difficult airways", Anaesthesia, vol. 70, No. 3, pp. 323-329, Mar. 2015.

*Primary Examiner* — Ellen C Hammond
(74) *Attorney, Agent, or Firm* — BakerHostetler (57) ABSTRACT

An apparatus for performing laryngoscopy is provided, the apparatus comprising a blade, a handle, and a medical gas supply device for provision of gas to a patient during laryngoscopy, wherein the medical gas supply device includes an outlet disposed on or in the handle of the device, or within the proximal half of the blade. A gas supply conduit supplies gas from a proximal aperture to outlet.

11 Claims, 7 Drawing Sheets

(56) References Cited

U.S. PATENT DOCUMENTS

| | | | | |
|---|---|---|---|---|
| 4,947,896 A * | 8/1990 | Bartlett | | A61B 1/267 |
| | | | | 600/187 |
| 6,106,458 A | 8/2000 | Ha | | |
| 7,608,040 B1 * | 10/2009 | Dunst | | A61B 1/012 |
| | | | | 600/187 |
| 7,946,981 B1 | 5/2011 | Cubb | | |
| 10,434,272 B1 * | 10/2019 | Annis | | A61M 16/0497 |
| 2001/0032646 A1 * | 10/2001 | Christopher | | A61M 16/0488 |
| | | | | 128/200.26 |
| 2007/0161863 A1 * | 7/2007 | Bentt | | A61B 1/267 |
| | | | | 600/187 |
| 2008/0105263 A1 * | 5/2008 | Jadhav | | A61B 1/015 |
| | | | | 128/207.15 |
| 2012/0022332 A1 * | 1/2012 | De Domenico | | A61B 1/267 |
| | | | | 600/194 |
| 2013/0296653 A1 * | 11/2013 | Brown | | A61M 16/0488 |
| | | | | 600/114 |
| 2014/0128676 A1 * | 5/2014 | Law | | A61B 1/00 |
| | | | | 600/114 |
| 2015/0099934 A1 * | 4/2015 | Sartore | | A61B 1/00091 |
| | | | | 600/187 |
| 2016/0256652 A1 * | 9/2016 | Wiesman | | A61M 16/0493 |
| 2016/0345803 A1 * | 12/2016 | Mallory | | A61B 1/00068 |
| 2017/0203070 A1 * | 7/2017 | Lei | | A61M 16/0666 |
| 2018/0214013 A1 * | 8/2018 | Casson | | A61B 1/05 |
| 2018/0228360 A1 * | 8/2018 | Shu | | A61B 1/00105 |
| 2018/0279867 A1 * | 10/2018 | Pecherer | | A61B 1/267 |
| 2019/0053698 A1 * | 2/2019 | Young | | A61B 1/267 |

FOREIGN PATENT DOCUMENTS

| | | |
|---|---|---|
| CN | 101647691 A | 2/2010 |
| CN | 103654705 A | 3/2014 |
| CN | 203885467 U | 10/2014 |
| CN | 204542041 U | 8/2015 |
| CN | 105231985 A | 1/2016 |
| EP | 2 653 093 A1 | 10/2013 |
| GB | 1 458 919 A | 12/1976 |
| GB | 2477084 A | 7/2011 |
| KR | 2012-0102197 A | 9/2012 |
| WO | 02/100238 A2 | 12/2002 |
| WO | 2007/081558 A2 | 7/2007 |

* cited by examiner

MEDICAL GAS DELIVERY SYSTEM

CROSS-REFERENCE TO RELATED APPLICATIONS

This application is a National Stage of International patent application PCT/GB2017/050506, filed on Feb. 24, 2017, which claims priority to Great Britain Patent Application No. GB 1603234.4, filed on Feb. 24, 2016, and Great Britain Patent Application No. 1608473.3, filed May 13, 2016, and the disclosures of which are incorporated by reference in their entireties.

During oral laryngoscopy a patient is normally not breathing but gas from the oral cavity and pharynx may be drawn into the trachea and to the lungs by a number of physiological processes, most importantly, apnoeic oxygenation and mass flow. Apnoeic oxygenation occurs because mammals normally absorb greater volumes of oxygen than the volumes of carbon dioxide gas that they excrete. This means that there is a net drawing in of gas from the mouth even if the mammal is not breathing. The two conditions for apnoeic oxygenation to occur are firstly the provision of oxygen in the upper airway and secondly an open airway or an open channel from the mouth to the lungs. During oral direct or indirect laryngoscopy this channel is normally kept substantially open and gas is therefore drawn into the mouth and towards the lungs. If oxygen enrichment is not used then this gas rapidly becomes mixed with air at 21% oxygen concentration.

To address this problem, oxygenation during laryngoscopy has been improved by allowing a continuous flow of oxygen at or into the mouth or directed to the pharynx or larynx at sufficient flows to replace the air with oxygen or to prevent air being drawn into the mouth. The delivery of oxygen to the oral cavity, pharynx, larynx and trachea is useful during laryngoscopy prior to tracheal intubation to improve both oxygenation and to extend the time available for placement of an endotracheal tube before the patient suffers an arterial oxygen desaturation. To achieve this, laryngoscope blades have included channels in their design to allow jetting or insufflation of gas or to allow suction to be applied. These have had narrow channels because they open to the patient's airway on the distal portion of the blade. A wide bore channel opening distally on the blade would risk impairing the view of the laryngoscopist or making, the blade unduly bulky thereby impairing it's insertion and function.

Thus, in the prior art, May describes in U.S. Pat. No. 4,126,127(A) a laryngoscope blade with an integral channel to supply oxygen to the larynx. The channel is at the distal tip of the blade and therefore necessarily has a small cross-sectional area.

Bentt describes in WO2007081558(A2) an oxygenating laryngoscope wherein the straight blade includes a conduit for attaching detachable tubing for delivery of oxygen to the airway during laryngoscopy. The tubing in this device extends to the distal end of the blade, requiring it to have a narrow bore and impeding laryngoscopic view and instrumentation.

An alternative approach to the problem of apnoeic oxygenation during laryngoscopy is that of replacing pharyngeal gases with oxygen by external nasal prongs using high flow gas delivery systems such as those described by Patel in the journal of the Association of Anaesthetists of Great Britain and Ireland, Anaesthesia (Anaesthesia, 2015 vol. 70(3) pp. 323-9). Although effective, this has the disadvantage of high costs, the requirement for very high oxygen flows and if the nasal passages are narrow or occluded it can become less effective.

It is therefore an object of the invention to seek to mitigate the problems of the prior art.

According to a first aspect of the invention there is provided apparatus for performing laryngoscopy, the apparatus comprising a blade, a handle and a medical gas supply device for provision of gas to a patient during laryngoscopy, wherein the medical gas supply device includes an outlet disposed on or in the handle of the device, or within the proximal half of the blade. As will be appreciated, the proximal end of the apparatus is the end that is nearest the user when the apparatus is in use in a patient. It has been found, surprisingly that the invention provides effective apnoeic oxygenation without obscuring the view of the anatomy even though the outlet is positioned, spatially, away from the area of required gas delivery.

The outlet may be disposed at or adjacent the proximal end of the blade. In another alternative, the outlet may be disposed in or on the distal half of the handle, the distal half being the half that is nearest the patient. It is most preferred that the outlet is disposed at or adjacent the distal end of the handle. These configurations result in minimal visual and physical obstruction whilst still providing effective apnoeic oxygenation.

It is preferred that the medical gas supply device is adapted to provide gas flow therefrom with substantially no entrainment of ambient air.

In one embodiment the medical gas supply device may be adapted to provide gas flow therefrom with substantially no entrainment of ambient air, by the outlet comprising a bore including a cross sectional area that is sufficiently large to substantially prevent the occurrence of a Venturi effect at or adjacent the blade. It is further preferred that the outlet comprises a bore including a cross sectional area that is sufficiently large to substantially prevent the occurrence of a Venturi effect at or adjacent the blade at medical gas flow rates of about 10 to 80 L/min, preferably up to 15 L/min.

In a further embodiment the medical gas supply device may be adapted to provide gas flow therefrom with substantially no entrainment of ambient air, by the outlet comprising a bore having a cross sectional area of from >about 3 mm sq to about 50 mm sq, preferably from about 3.5 mm sq to about 20 mm sq, most preferably from about 4 mm sq to about about 12.5 mm sq. Although an outlet with a small cross sectional area and/or fine bore gas supply tubing has an advantage of not impeding laryngoscopic view unduly and not making the apparatus bulky there is a disadvantage that at high gas flow velocity, a small cross sectional area outlet will cause ambient air to be entrained alongside the medical gas being delivered by a mechanism related to the Venturi effect, thereby diluting the concentration of medical gas being delivered considerably. Experimentally and from the principles of physics it can be determined that at typical medical gas flow rates a larger cross sectional area outlet placed, for example, on the proximal portion of the blade (near the mouth opening during a laryngoscopy) will not impair the laryngoscopic view, nor make the blade unduly bulky in the middle or distal portion so as not to impede placement into the patient's airway, whilst minimising the Venturi effect, thereby flooding the airway with high concentrations of oxygen for the purpose of optimising apnoeic oxygenation.

In a further embodiment the medical gas supply device may be adapted to provide gas flow therefrom with substantially no entrainment of ambient air, by the apparatus comprising a plurality of outlets.

Thus it can be seen that the invention is a gas delivery device that allows the delivery of a medical gas to the laryngeal and pharyngeal airway. The device may comprise a hollow tube or conduit with a proximal end for attachment to a pressurised medical gas supply source, such as a medical oxygen flowmeter, and a distal end for release of the gas substantially at the mouth of a patient or, in another embodiment, it extends inside the mouth or pharynx to release gas at these locations. The aperture of the distal tubing in the invention is preferably on the proximal half of the laryngoscope blade and/or at or adjacent the distal end of a laryngoscope handle such that it does not impair vision during laryngoscopy. Blade designs allowing the aperture opening more distally are possible but the lumen must be sufficiently large to prevent a significant Venturi effect. As the distal aperture is located at the proximal end of a laryngoscope blade or at the distal end of a laryngoscope handle, it is possible to use a much wider aperture bore than is possible for gas delivery apertures located at the distal tip of the laryngoscope blade. This is advantageous as it provides a greater oxygen flow to a patient's laryngeal and pharyngeal airway without blocking the view of the distal tip of a laryngoscope blade.

Preferably, the gas delivery device comprises an attachment element adapted to reversibly attach the gas delivery device to the laryngoscope blade or handle. This is advantageous in situations where an intubation proves to be complex and difficult. In this situation, a gas delivery device can be attached to a laryngoscope to ensure a flow of medical gas during the procedure, particularly if the procedure has taken a long period of time. The gas delivery device being reversibly detachable may also be advantageous in that it allows ease of cleaning and sterilisation of the laryngoscope and the gas delivery device.

Preferably, the gas delivery device is permanently connected to the proximal end of the laryngoscope blade or the distal end of the laryngoscope handle. This is advantageous in situations where it is known that a medical gas flow will be required during a laryngoscopy. The permanently connected gas delivery device may preferably be integral to the laryngoscope blade or the laryngoscope handle.

According to a second aspect of the invention there is provided a method of conducting a laryngoscopy, the method comprising the step of using apparatus as defined hereinabove.

The present invention will now be described, by way of example only, with reference to the accompanying drawings, in which.

Figure 1A:
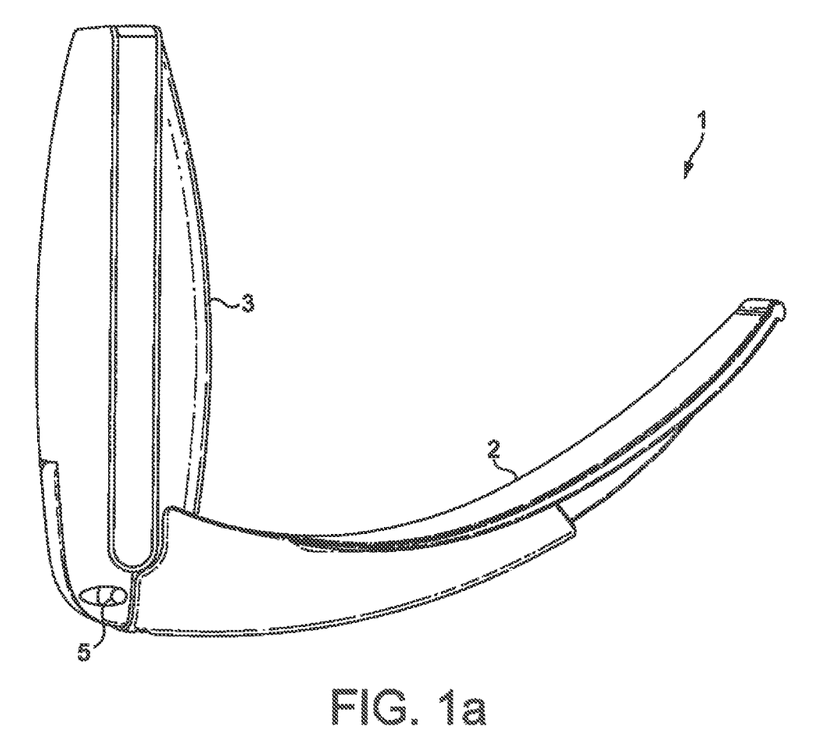
FIGS. 1a and 1b are schematic side views of apparatus according to the invention.
Figure 1B:
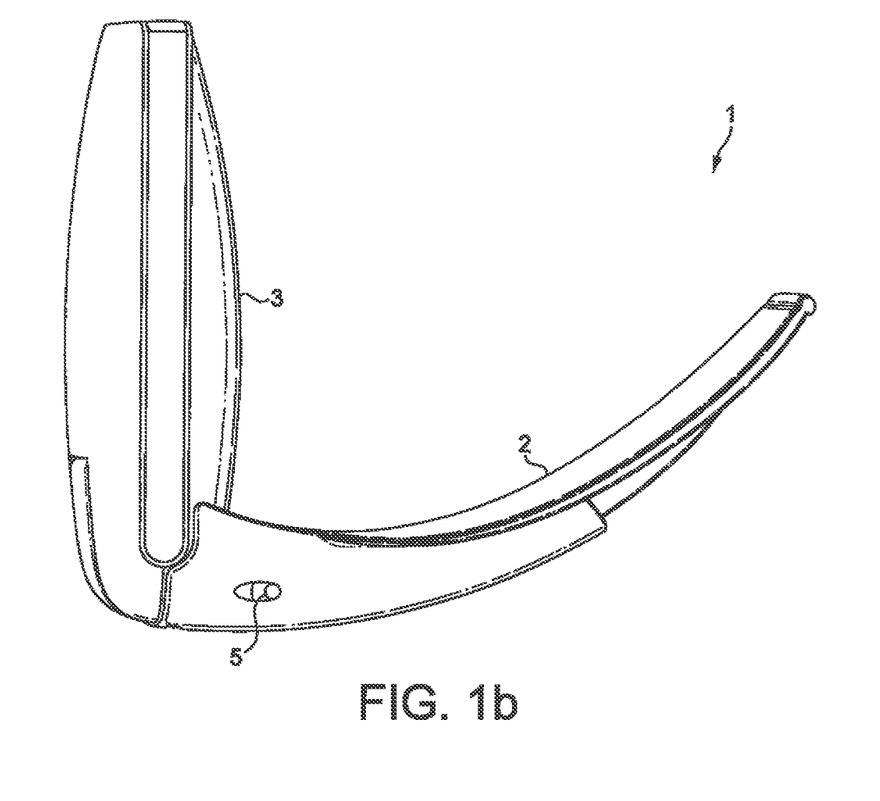
Figure 1C:
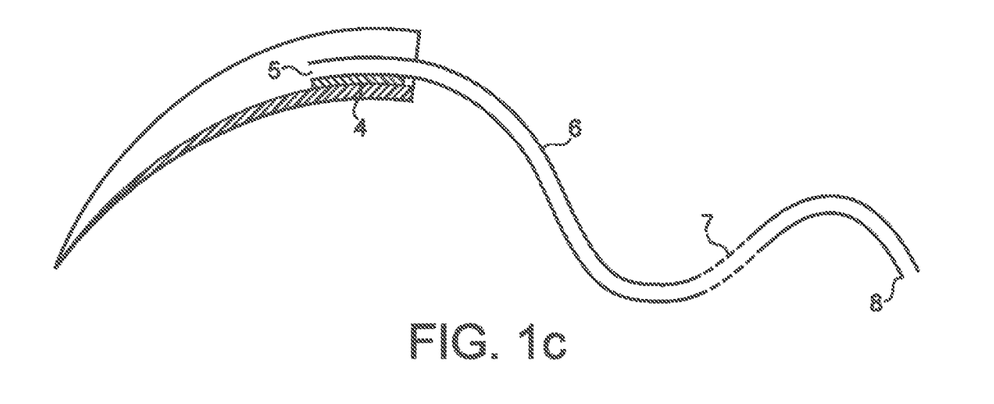
FIG. 1c is a schematic side view of a part of the apparatus of FIG. 1b.

Referring to the Figures and in particular FIGS. 1a to 1c, there is illustrated apparatus 1 for performing laryngoscopy, the apparatus comprising a blade 2, a handle 3 and a medical gas supply device 4 for provision of gas to a patient during laryngoscopy, wherein the medical gas supply device 4 includes an outlet 5 disposed on or in the handle of the device, or within the proximal half of the blade, A gas supply conduit 6 supplies gas from a proximal aperture 8 to outlet 5.

In FIG. 1c, proximal aperture 8 is designed to attach securely on a standard oxygen flowmeter outlet. Wide (for example 3 mm-10 mm internal diameter) tubing carries oxygen in a low resistance pathway, conduit 6. Reference numeral 7 represents an artificial break as the proximal portion will be long (for example over 1 meter long) to reach an oxygen source conveniently. This section of the conduit 6 represented by reference numeral 7 may be reversibly coiled for convenient storage and use.

An attachment element or a permanent attachment means is preferably at the proximal third of the laryngoscope blade 2.

The crossectional lumen area at outlet 5 and proximal to the distal aperture is a wide bore aperture to prevent high gas velocity at the aperture and resulting entrainment of air into the patient's distal airway at the tip of the blade 2.

As can be appreciated from FIGS. 1a to 1c, line of sight and instrumentation are not substantially impeded by the outlet 5 or conduit 6. Locating the outlet 5 at the proximal end of a laryngoscope blade or at the distal end of a laryngoscope handle 3 does not obstruct the view of the distal tip of the laryngoscope blade 2. Therefore, the wider bore of outlet 5 and conduit 6 makes it possible to deliver medical gas much more effectively than for delivery apertures placed in the distal tip of a laryngoscope blade.

In one embodiment, the outlet 5 for gas delivery may be disposed on the lower, in use, surface of the laryngoscope blade 2, the lower surface of the laryngoscope blade being the surface not in contact with the tongue during a laryngoscopy procedure.

The outlet 5 of the gas delivery device is adapted to direct a jet of gas into the pharynx or larynx. In one embodiment, the outlet 5 for gas delivery may be positioned on the apparatus such that it is positioned outside of the patient's mouth in normal usage but, when in use, directs gas into the mouth. The gas delivery device 4 may be attached to the laryngoscope blade or the handle of the laryngoscope but positioned such that it sits outside of but substantially proximate the opening of the mouth.

In a preferred embodiment, the outlet 5 of the gas delivery device 4 is located in the proximal third of the laryngoscope blade 2 so as to not impair vision or instrumentation of the airway distally. In one embodiment of the invention the outlet 5 is greater than 7 mm sq. in cross-sectional area. In another embodiment, the outlet 5 is circular in cross-sectional shape and in one embodiment it is non-circular in cross-sectional shape. In yet another embodiment, the cross-sectional area of the outlet 5 is 20 square millimetres. Other embodiments of the invention have an outlet 5 of cross-sectional area greater than 20 square millimetres.

In one embodiment, the gas delivery device 4 may include multiple outlets 5 with aperture sizes and resistances to allow flow in multiple directional streams of gas. In another embodiment, the gas delivery device has a narrow cross sectional bore tubing but the distal portion is designed with multiple apertures or directional apertures so as to reduce jet like flow and reduce the Venturi effect.

In one embodiment, the invention comprises a conduit 6 with a resistance to flow such that at a pressure of approximately 4 atmospheres at the proximal end, flow is restricted to a known safe rate. Four atmospheres is conventionally the oxygen pressure in hospital piped oxygen systems and in full oxygen cylinders. For example, the resistance to flow could be manufactured to be such that at a pressure of 4 atmospheres a rate of 60 L/min is achieved or in another embodiment 30 L/min would be achieved or in another embodiment 15 L</min would be achieved. This would allow a user to open up a flowmeter completely and be prevented from applying unduly and potentially dangerous flow rates.

In one embodiment, the gas delivery device 4 includes a port in the conduit 6 with a one way valve to allow injection of fluid, for example local anaesthetic solution, to facilitate application to the airway.

In one embodiment, the invention comprises delivery tubing (conduit 6) being curled like a spring or coil such that when the laryngoscope blade 2 is moved distant from the proximal connection to the oxygen source tidy extension of the tube is facilitated and when the laryngoscope blade is moved closer to the oxygen source the coil reforms thereby preventing tangling or the tubing getting in the way of the laryngoscopist or assistants.

In one embodiment, the gas delivery device 4 reversibly attaches to either the laryngoscope blade or laryngoscope handle 2. The mechanism of attachment can be of many types including a slip which wedges onto and grips the blade edge. It is desirable for the slip to be secure but non-traumatic to the tongue. In another embodiment, the attachment mechanism uses a piece of adhesive tape attached to the distal end of the tubing near the outlet 5 to tape the invention to a laryngoscope blade 2 at or near conduit 6. Many laryngoscope blades have a convenient flat surface on the back (opposite end to the tip) of the blade to which a sleeve or adhesive tape may conveniently and securely reversibly fasten. In yet another embodiment, the gas delivery device 4 comprises one or more magnet or ferromagnetic element in the handle or blade or a combination of the two to allow reversible attachment of a magnetic or ferromagnetic element on the invention. In a further embodiment, the gas delivery device comprises an element near the distal aperture that reversibly or irreversibly connects to a paired fixation element on a laryngoscope blade 2.

In one embodiment, the gas delivery device 4 has the supply conduit 6 and outlet 5 permanently connected to the proximal half of the laryngoscope blade and preferably the proximal third of the laryngoscope blade 2.

One embodiment of the device may be combined with a laryngoscope handle or blade covering.

The gas delivery device 4 may comprise a proximal portion and a distal portion. In one embodiment, the gas delivery device 4 is flexible in the distal portion. In another embodiment the gas delivery device 4 is rigid in the distal portion. In yet another embodiment, the gas delivery device 4 has flexible elements and rigid elements. One embodiment having a flexible element connecting the device to the oxygen source, a rigid element adjacent to the laryngoscope handle and a rigid or flexible element near or adjacent to the laryngoscope blade surface.

A preferred embodiment of the invention is single use and disposable so cleaning for reuse is not an issue.

Experiment A

Figure 2:
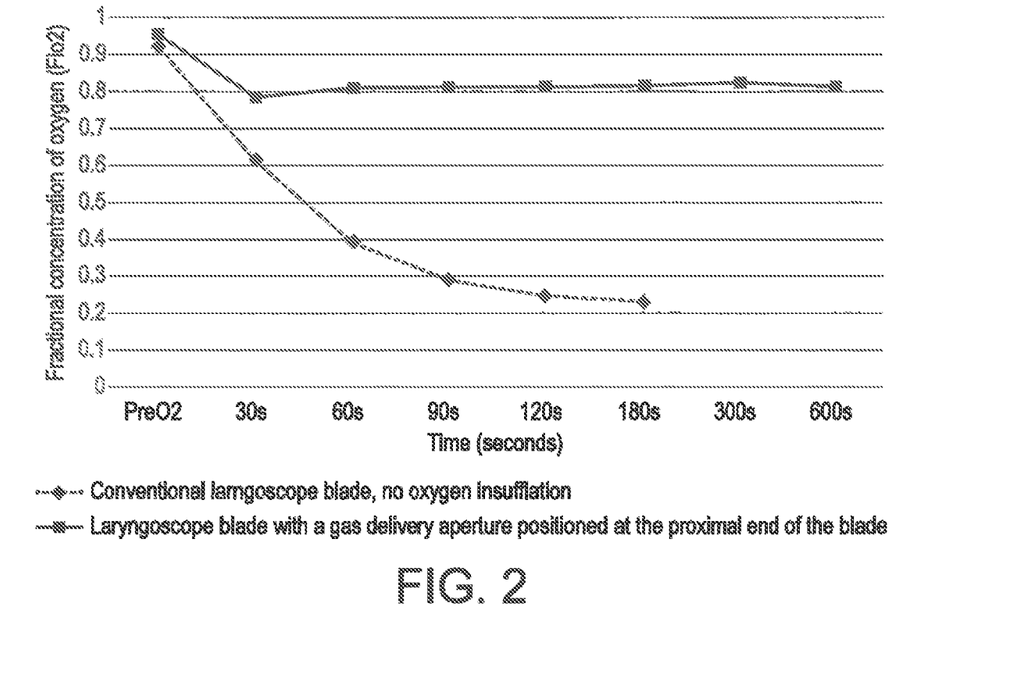
FIG. 2 shows a graph of the difference between the airway FiO2 concentration during laryngoscopy when performed using a conventional laryngoscope blade (no oxygen insufflation) and when performed using a laryngoscope blade with a gas delivery aperture positioned at the proximal end of the blade.

FIG. 2 shows the results of an experiment in which the fraction of inspired oxygen (FiO2) was monitored during laryngoscopy from preintubation to 600 seconds. The experiment was performed using a conventional laryngoscope blade, with no oxygen insufflation, and a laryngoscope blade with a gas delivery outlet 5 at the proximal end of the blade.

TABLE 1

Changes in FiO2 over a 10 minute period during laryngoscopy using a conventional laryngoscope blade, with no oxygen insufflation, and a laryngoscope blade fitted with a gas delivery aperture positioned at the proximal end of the blade.

|  | PreO2 | FiO2 @ 30 s | FiO2 @ 60 s | FiO2 @ 90 s | FiO2 @ 120 s | FiO2 @ 180 s | FiO2 @ 300 s | FiO2 @ 600 s |
|---|---|---|---|---|---|---|---|---|
| Conventional Larngoscope Blade, no oxygen insufflation | 0.923 | 0.616 | 0.394 | 0.289 | 0.246 | 0.23 | | |
| Laryngoscope blade with a gas delivery aperture positioned at the proximal end of the blade | 0.955 | 0.786 | 0.812 | 0.813 | 0.814 | 0.816 | 0.826 | 0.815 |

As is shown in Table 1 and FIG. 2, when compared to a conventional laryngoscope blade, the laryngoscope blade with a gas delivery outlet 5 located at the proximal end of the blade shows a markedly increased concentration of FiO2 during the entire period of monitoring.

Experiment B

Figure 3:
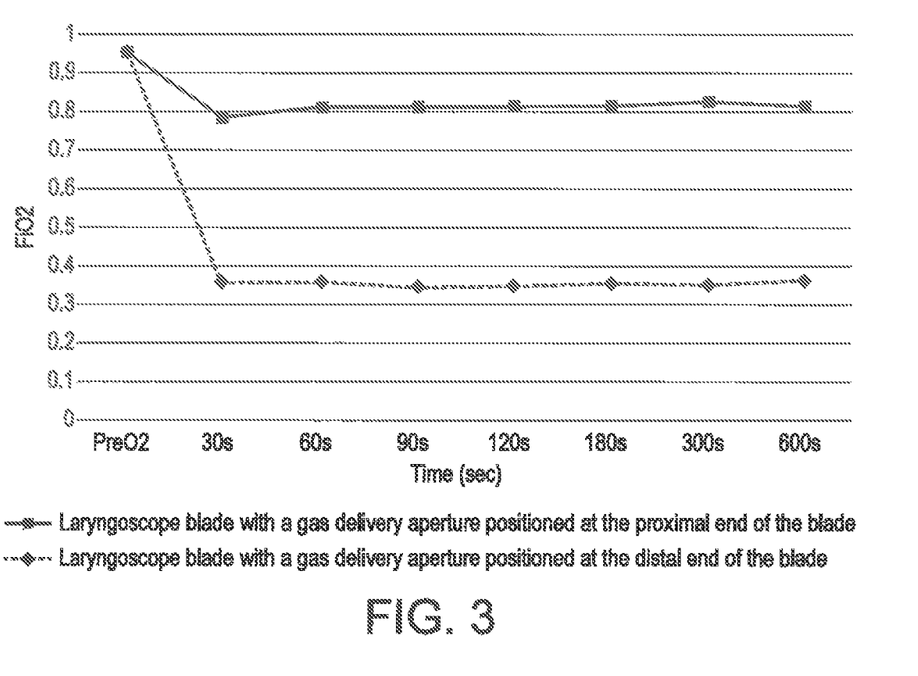
FIG. 3 shows a graph of the difference between the airway FiO2 concentration during laryngoscopy when performed using a laryngoscope blade with a gas delivery aperture positioned at the proximal end of the blade and when performed using a laryngoscope blade with a gas delivery aperture positioned at the distal end of the blade.

FIG. 3 shows the results of an experiment in which a gas delivery device was attached to either the proximal end or distal end of a laryngoscope blade. For the version of the laryngoscope blade in which the outlet 5 was located at the proximal end of the laryngoscope blade, the gas delivery device comprised a wide bore distal aperture. For the version of the laryngoscope blade in which the outlet 5 was located at the distal end of the laryngoscope blade, the gas delivery device comprised the widest bore of tubing that could be used without obstructing the view of the distal tip of the laryngoscope blade. FiO2 was monitored during laryngoscopy from preintubation to 600 seconds.

TABLE 2

Changes in FiO2 over a 10 minute period during laryngoscopy using a laryngoscope blade with gas delivery aperture located at the proximal end of the blade.

| Experiment Number | FiO2 after preO2 | FiO2 @ 30 s | FiO2 @ 60 s | FiO2 @ 90 s | FiO2 @ 120 s | FiO2 @ 3 min | FiO2 @ 5 min | FiO2 @ 10 min |
|---|---|---|---|---|---|---|---|---|
| 1 | 95 | 76 | 77 | 77 | 77 | 77 | 77 | 81 |
| 2 | 95 | 80 | 84 | 83 | 84 | 82 | 88 | 83 |
| 3 | 95 | 74 | 74 | 76 | 79 | 78 | 78 | 78 |
| 4 | 95 | 80 | 84 | 82 | 83 | 86 | 85 | 82 |
| 5 | 96 | 74 | 81 | 83 | 81 | 83 | 80 | 80 |
| 6 | 95 | 81 | 84 | 82 | 81 | 83 | 81 | 80 |
| 7 | 98 | 77 | 82 | 82 | 79 | 80 | 84 | 80 |
| 8 | 96 | 81 | 80 | 79 | 80 | 80 | 80 | 82 |
| 9 | 95 | 81 | 83 | 83 | 85 | 82 | 87 | 86 |
| 10 | 95 | 82 | 83 | 86 | 85 | 85 | 86 | 83 |
| Average Value | 95.5 | 78.6 | 81.2 | 81.3 | 81.4 | 81.6 | 82.6 | 81.5 |

TABLE 3

Changes in FiO2 over a 10 minute period during laryngoscopy using a laryngoscope blade with gas delivery aperture located at the distal end of the blade.

| Experiment Number | FiO2 after preO2 | FiO2 @ 30 s | FiO2 @ 60 s | FiO2 @ 90 s | FiO2 @ 120 s | FiO2 @ 3 min | FiO2 @ 5 min | FiO2 @ 10 min |
|---|---|---|---|---|---|---|---|---|
| 1 | 96 | 35 | 34 | 35 | 36 | 35 | 34 | 36 |
| 2 | 96 | 36 | 36 | 35 | 35 | 34 | 34 | 34 |
| 3 | 96 | 32 | 33 | 34 | 33 | 34 | 35 | 34 |
| 4 | 96 | 32 | 33 | 32 | 33 | 32 | 35 | 37 |
| 5 | 96 | 36 | 36 | 36 | 34 | 35 | 34 | 37 |
| 6 | 97 | 38 | 36 | 36 | 35 | 37 | 34 | 38 |
| 7 | 97 | 38 | 37 | 34 | 34 | 36 | 36 | 34 |
| 8 | 96 | 34 | 33 | 34 | 35 | 38 | 34 | 37 |
| 9 | 95 | 40 | 40 | 34 | 35 | 36 | 37 | 37 |
| 10 | 96 | 40 | 39 | 34 | 36 | 36 | 36 | 37 |
| Average Value | 96.1 | 36.1 | 35.7 | 34.4 | 34.6 | 35.3 | 34.9 | 36.1 |

Table 2 shows the results from 10 intubations using the laryngoscope blade with a gas outlet 5 at the proximal end of the blade and Table 3 shows the results from 10 intubations using the laryngoscope blade with a gas outlet 5 at the distal end of the blade. As is shown in FIG. 3, the laryngoscope blade with a gas outlet 5 at the proximal end of the blade shows a markedly increased concentration of FiO2 during the entire period of monitoring.

Experiment C

Figure 4:
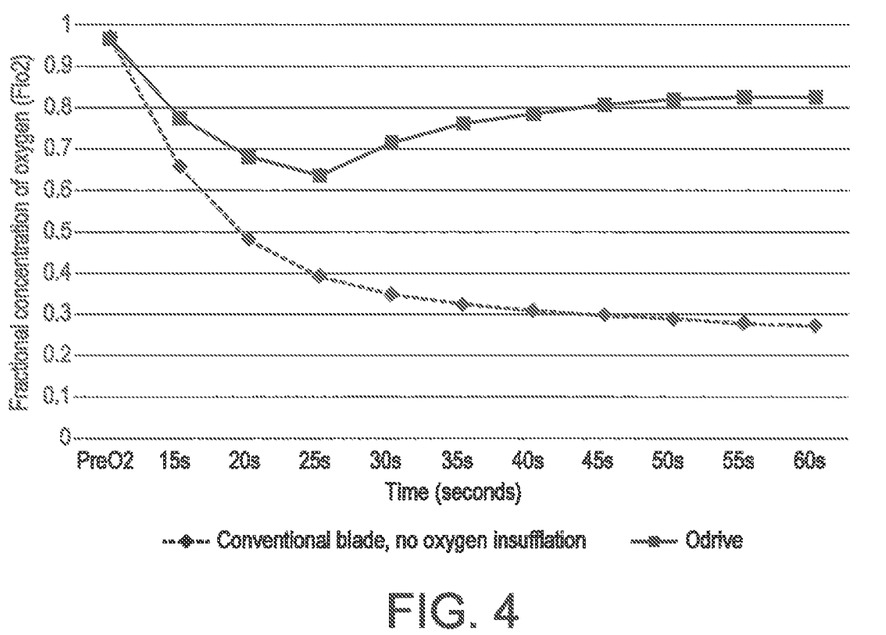
FIG. 4 shows a graph of the difference between FiO2 concentration during laryngoscopy after the application of pharyngeal suctioning when performed using a conventional laryngoscope blade, with no oxygen insufflation, and when performed using a laryngoscope blade fitted with a gas delivery aperture positioned at the proximal end of the blade.

FIG. 4 shows the results of an experiment in which the FiO2 concentration was monitored over 60 seconds during laryngoscopy where pharyngeal suctioning was applied during the procedure. Pharyngeal suctioning may be required during a laryngoscopy to enable a clear view of the laryngeal and pharyngeal airway such that the medical professional can accurately insert an endotracheal tube. Pharyngeal suctioning can be of vital importance during a laryngoscopy if there has been trauma and blood and vomitus are obscuring the laryngeal and pharyngeal airways. As will be appreciated, ensuring as high a FiO2 concentration during such difficult intubations is critical. Laryngoscopy was performed using either a conventional laryngoscope blade, with no oxygen insufflation, or a laryngoscope blade fitted with a gas outlet 5 at the proximal end of the laryngoscope blade.

TABLE 4

Changes in FiO2 during laryngoscopy after the application of pharyngeal suctioning using a conventional laryngoscope blade, with no oxygen insufflation, and a laryngoscope blade fitted with a gas delivery aperture located at the proximal end of the blade.

| | PreO2 | 15 s | 20 s | 25 s | 30 s | 35 s | 40 s | 45 s | 50 s | 55 s | 60 s |
|---|---|---|---|---|---|---|---|---|---|---|---|
| Conventional Blade, no oxygen insufflation | 0.972 | 0.658 | 0.481 | 0.391 | 0.346 | 0.322 | 0.307 | 0.295 | 0.286 | 0.276 | 0.27 |
| Laryngoscope blade with a gas delivery aperture | 0.966 | 0.775 | 0.681 | 0.636 | 0.716 | 0.762 | 0.785 | 0.807 | 0.82 | 0.825 | 0.826 |

TABLE 4-continued

Changes in FiO2 during laryngoscopy after the application of pharyngeal suctioning using a conventional laryngoscope blade, with no oxygen insufflation, and a laryngoscope blade fitted with a gas delivery aperture located at the proximal end of the blade.

| | PreO2 | 15 s | 20 s | 25 s | 30 s | 35 s | 40 s | 45 s | 50 s | 55 s | 60 s |
|---|---|---|---|---|---|---|---|---|---|---|---|
| positioned at the proximal end of the blade | | | | | | | | | | | |

Table 4 and FIG. 4 show that the FiO2 concentration of the laryngoscope blade with a gas outlet 5 at the proximal end of the laryngoscope blade was far higher than when using a conventional laryngoscope blade and actually rebounded to a level close to the FiO2 concentration prior to pharyngeal suctioning.

Experiment D

Figure 5:
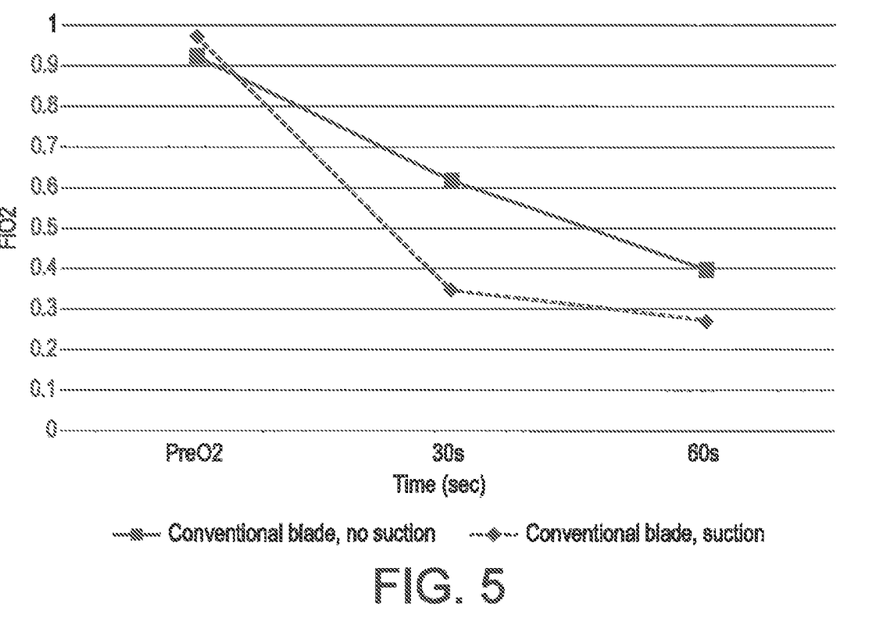
FIG. 5 shows a graph of the difference between FiO2 during laryngoscopy with and without 10 seconds of suction when performed using a conventional laryngoscope blade, with no oxygen insufflation.
Figure 6:
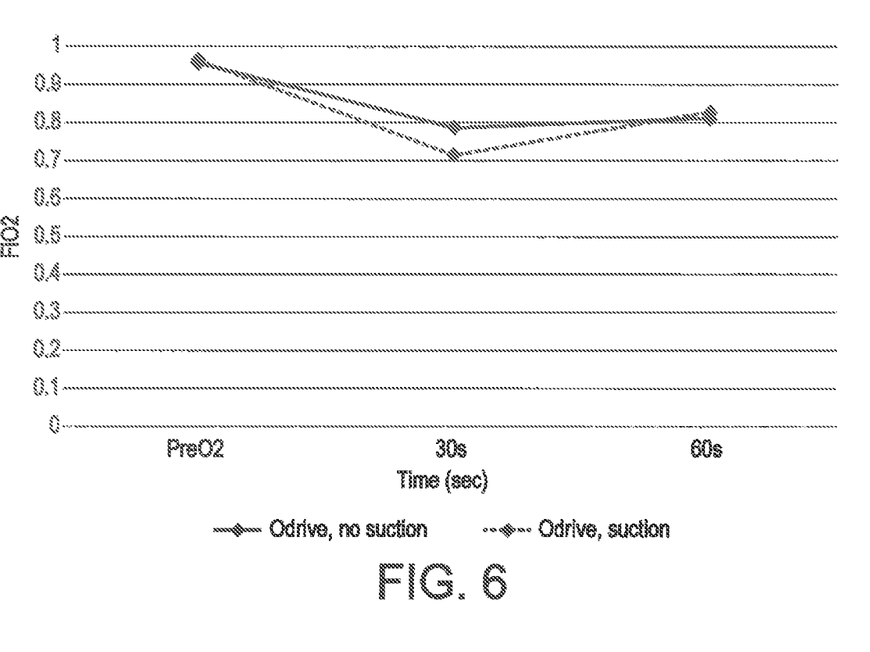
FIG. 6 shows a graph of the difference between FiO2 during laryngoscopy with and without 10 seconds of suction when performed using a laryngoscope blade fitted with a gas delivery aperture positioned at the proximal end of the blade.

FIGS. 5 and 6 show the results of an experiment to determine the effects of suction verses no suction on FiO2 concentration when using a conventional laryngoscope blade, with no oxygen insufflation, and a laryngoscope blade fitted with a gas outlet 5 located at the proximal end of the laryngoscope blade. Where suction was applied, pharyngeal suctioning was applied for 10 seconds.

TABLE 5

Changes in FiO2 over a 60 second period during laryngoscopy with and without 10 seconds of suction using a conventional laryngoscope blade, with no oxygen insufflation, and during laryngoscopy with and without suctions using a laryngoscope blade fitted with a gas delivery aperture positioned at the proximal end of the blade.

| | PreO2 | 30 s | 60 s |
|---|---|---|---|
| Conventional Blade, no suction | 0.923 | 0.616 | 0.394 |
| Conventional blade, suction | 0.972 | 0.346 | 0.27 |
| Laryngoscope blade with a gas delivery aperture positioned at the proximal end of the blade, no suction | 0.955 | 0.786 | 0.812 |
| Laryngoscope blade with a gas delivery aperture positioned at the proximal end of the blade, suction | 0.966 | 0.716 | 0.826 |

As shown by Table 5 and FIGS. 5 and 6, pharyngeal suctioning dramatically reduced the FiO2 concentration for the conventional laryngoscope blade but overall FiO2 concentration decreased substantially over time as previously shown in Experiments A and C. However, while suctioning decreased the FiO2 concentration for the laryngoscope blade fitted with a gas outlet 5 at the proximal end of the laryngoscope blade, the FiO2 concentration rebounded to the same concentration that was seen when no suction was applied during laryngoscopy.

The invention claimed is:

1. An apparatus for performing laryngoscopy, the apparatus comprising a blade, a handle and a medical gas supply device for provision of gas to a patient during laryngoscopy, wherein the blade has a distal end and a proximal end, wherein the medical gas supply device includes an outlet disposed on or in a distal half of the handle of the apparatus, or at or adjacent a proximal end of the external surface of the blade, wherein the outlet is positioned such that it is proximate the opening of a patient's mouth and directs gas into the mouth.

2. The apparatus according to claim 1, wherein the outlet is disposed at or adjacent the distal end of the handle.

3. The apparatus according to claim 1, the outlet comprising a bore including a cross sectional area that is adapted to prevent the occurrence of a Venturi effect at or adjacent the blade.

4. The apparatus according to claim 3, wherein the outlet comprises a bore including a cross sectional area that is adapted to prevent the occurrence of a Venturi effect at or adjacent the blade at oxygen flow rates of about 10 to 80 L/min.

5. The apparatus of claim 4, wherein the oxygen flow rate is up to 15 L/min.

6. The apparatus according to claim 1, the outlet comprising a bore having a cross sectional area of from about 3 mm sq. to about 50 mm sq.

7. The apparatus of claim 6, wherein the bore has a cross sectional area from about 3.5 mm$^2$ to about 20 mm$^2$.

8. The apparatus of claim 7, wherein the bore has a cross sectional area from about 4 mm$^2$ to about 12.5 mm$^2$.

9. The apparatus according to claim 1, wherein the outlet is non-circular in cross-sectional shape.

10. The apparatus according to claim 1, wherein the outlet is disposed on or in a lower, in use, surface of the blade.

11. A method of conducting a laryngoscopy, the method comprising supplying oxygen to a patient via an apparatus of claim 1.

* * * * *